United States Patent
Suzuki et al.

(10) Patent No.: US 9,019,490 B2
(45) Date of Patent: *Apr. 28, 2015

(54) SURFACE-DEFECT INSPECTION DEVICE

(71) Applicant: Hitachi High-Technologies Corporation, Ibaraki (JP)

(72) Inventors: Katsuya Suzuki, Hitachinaka (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/956,858

(22) Filed: Aug. 1, 2013

(65) Prior Publication Data

US 2013/0314700 A1 Nov. 28, 2013

Related U.S. Application Data

(63) Continuation of application No. 13/390,342, filed as application No. PCT/JP2010/065781 on Sep. 14, 2010, now Pat. No. 8,547,546.

(30) Foreign Application Priority Data

Sep. 30, 2009 (JP) ................. 2009-227873

(51) Int. Cl.
G01N 21/00 (2006.01)
G01N 21/93 (2006.01)
G01N 21/95 (2006.01)
G01N 21/88 (2006.01)
H04N 5/77 (2006.01)
H04L 9/32 (2006.01)

(52) U.S. Cl.
CPC ........ G01N 21/93 (2013.01); *G01N 2021/8861* (2013.01); G01N 21/9501 (2013.01); *H04N 5/77* (2013.01); *H04L 9/3247* (2013.01)

(58) Field of Classification Search
None
See application file for complete search history.

(56) References Cited

U.S. PATENT DOCUMENTS 7,426,031 B2 9/2008 Kim et al.
7,528,944 B2 * 5/2009 Chen et al. ................. 356/237.6

(Continued)

FOREIGN PATENT DOCUMENTS

JP 8-219943 8/1996
JP 2004-295879 10/2004

(Continued)

OTHER PUBLICATIONS

Office Action in JP 2009-227873, mailed Dec. 4, 2012, (in Japanese, 1 pg.) [including English language translation, 1 pg.].

*Primary Examiner* — Kara E Geisel
*Assistant Examiner* — Amanda Merlino
(74) *Attorney, Agent, or Firm* — Baker Botts L.L.P.

(57) ABSTRACT

A data processing and controlling portion calculates the amounts of coordinate deviations between artificial defects on a standard sample and detected defects on an inspected sample, checks the sensitivity (instrumental sensitivity (luminance, brightness, or the like)), and proceeds to execution of hardware corrections. If the coordinate deviation is less than a certain value, software corrections are carried out. In the case of the software corrections, coordinate corrections are made for the whole standard sample. The amounts of coordinate deviations are computed and checked. If the amounts of coordinate deviations are outside a tolerance, coordinate corrections are made for each region obtained by dividing the standard sample.

17 Claims, 9 Drawing Sheets

(56) References Cited

U.S. PATENT DOCUMENTS 7,675,613 B2 3/2010 Nakao et al.
2009/0195775 A1* 8/2009 Nakao et al. ............... 356/237.2

FOREIGN PATENT DOCUMENTS

| JP | 2006-145269 | 6/2006 |
|----|-------------|--------|
| JP | 2009-180691 | 8/2009 |

* cited by examiner

SURFACE-DEFECT INSPECTION DEVICE

CROSS-REFERENCE TO RELATED APPLICATIONS

This application is a continuation application of U.S. application Ser. No. 13/390,342, filed Feb. 14, 2012, and which application is a §371 National Stage application of PCT/JP-2010/065781, filed Sep. 14, 2010, the entire contents of which are incorporated herein.

TECHNICAL FIELD

The present invention relates to an optical surface-defect inspection device and surface-defect inspection method for inspecting foreign matter, defects, or the like on a surface of an inspected object during manufacturing steps for semiconductor devices or the like.

BACKGROUND ART

The accuracy of the coordinates of each defect detected by optical defect inspection device is important performance, for example, in identifying defective parts on a semiconductor device, observing the defects with a review device, classifying the defects, and making a decision as to whether each defect is good or not. In recent years, as semiconductor devices have been manufactured with ever decreasing sizes, the requirements for defect coordinate accuracy have become more stringent year by year.

In the conventional optical defect inspection device, actual foreign matter has been used in identifying or correcting the positions of defects and making corrections to the coordinates at which defects are detected for observations with a defect review device. In the conventional coordinate correction method, the amount of deviation in the direction of rotation, the amount of elongating or contracting deviation, the amount of deviation of conveyance, and the amount of deviation of an optical axis are calculated, and a correction is made using the whole object to be inspected.

With the conventional technique of review devices, it is customary that coordinate corrections are made for defects of somewhat large size by the use of known defects and then fine corrections are made for defects of smaller sizes and that the coordinates of the review device are corrected.

As described in patent literatures, it is usual that defect sizes and positions are forecasted based on the results of detection of defects made by a defect inspection device and a correction is made on the side of the review device such that defects can be quickly brought to within the screen and captured.

Furthermore, based on the position of a defect on an inspected object observed with a review device, the same inspected object is inspected by a defect inspection device, the coordinates are corrected from the results of the inspection, and then a different sample is inspected.

Based on the results of an inspection of a different sample made by the defect inspection device, defects are observed with the review device. In practice, however, coordinate corrections are again made in conformity with actual defects by the review device.

CITATION LIST

Patent Literatures

Patent literature 1: JP-A-2006-145269

SUMMARY OF INVENTION

Technical Problem

In an optical defect inspection device, there is a demand for improvement of the defect coordinate accuracy. There exists the problem that with the total coordinate correction of the inspected object, errors in individual regions (due to undulation of the sample or the like) cannot be fully corrected.

It is an object of the present invention to realize surface-defect inspection device and surface-defect inspection method capable of improving the accuracy of the coordinates of defects and reducing errors in the coordinates of detected defects.

Solution to Problem

In order to achieve the above-described object, the present invention is configured as follows.

In surface-defect inspection device and surface-defect inspection method, a standard sample on which defects of known coordinates have been previously formed is illuminated with illuminating light. Scattering light from the standard sample is detected, and the image coordinates of the defects on the surface are corrected. Based on the corrected image coordinates, defects on the surface of the inspected object are inspected.

Advantageous Effects of Invention

Surface-defect inspection device and surface-defect inspection method capable of improving the accuracy of the coordinates of defects and reducing errors in the coordinates of the detected defects can be accomplished.

Other objects, features, and advantages of the present invention will be apparent from the following description of the embodiments of the present invention provided in connection with the accompanying drawings.

DESCRIPTION OF EMBODIMENTS

Embodiments of the present invention are hereinafter described with reference to the accompanying drawings.

Embodiment 1

Figure 1:
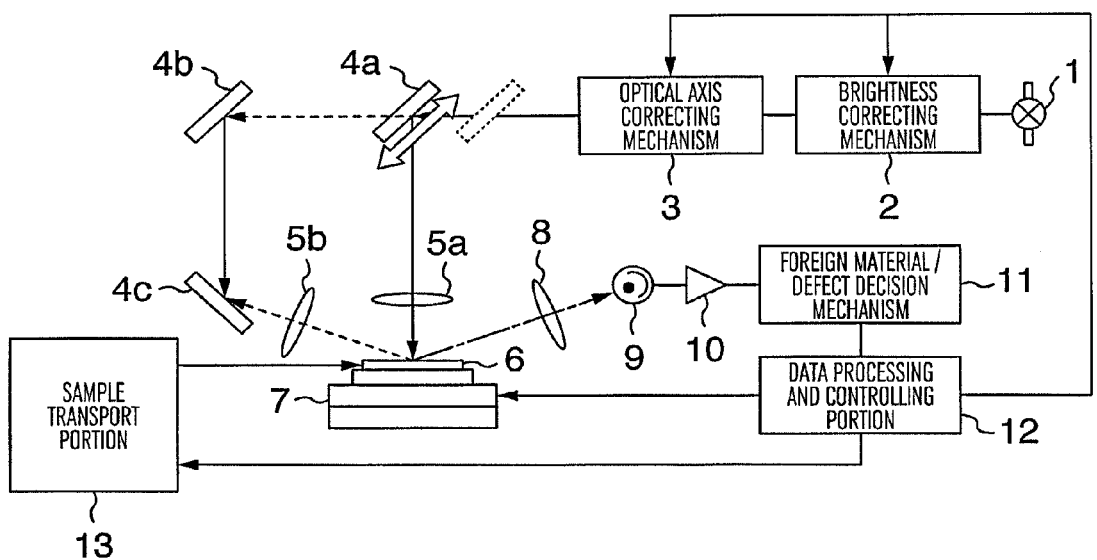
FIG. 1 is a schematic block diagram of an optical defect inspection device to which the present invention is applied.

FIG. 1 is a schematic block diagram of an optical surface-defect inspection device that is embodiment 1 of the present invention.

In FIG. 1, light emitted from a light source 1 passes through a light amount adjusting mechanism 2 capable of adjusting the brightness and through an optical axis correcting mechanism 3 and is made to hit an inspected object 6 via a mirror 4a and a condenser lens 5a. The light emitted from the light source 1 also passes through the light amount adjusting mechanism 2 and the light axis correcting mechanism 3 and is made to hit the inspected object 6 via the mirror 4a, a mirror 4b, a mirror 4c, and a condenser lens 5b.

The inspected object 6 is disposed on an XZ seater stage 7 having a rotary stage, a straight motion X stage, and a heightwise direction Z stage. Scales permitting one to know positional coordinates are disposed on the stages, respectively.

Furthermore, the defect inspection device has a foreign material/defect decision mechanism 11 for recording the coordinates of positions at which scattering light from defects on the inspected object 6 is detected from the scales of the stage 7 and for computing the coordinates of the defects, as well as a data processing and controlling portion 12 for correcting the positions of the defects. In addition, the defect inspection device is equipped with a sample transport portion 13 for moving the stage 7 in accordance with an instruction signal from the data processing and controlling portion 12.

Light scattered from the inspected object 6 is sent to the foreign material/defect decision mechanism 11 via a lens 8, a detector 9, and an amplifier 10.

The data processing and controlling portion 12 analyzes the positions, sizes, and shapes of defects on the inspected object 6 from the aforementioned stage position and from scattering light data.

The data processing and controlling portion 12 corrects the detected coordinates and provides feedback control of the mechanisms, i.e. stage 7, brightness correcting mechanism 2, and light axis correcting mechanism 3, to thereby control their operations and provide an output indicative of ultimate defect information about the inspected object 6.

Figure 2:
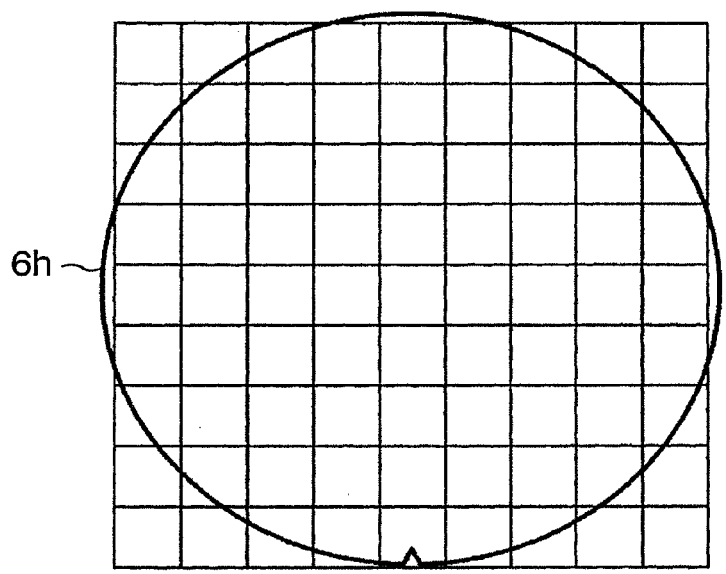
FIG. 2 is a view showing an example of how a standard sample is divided into regions in embodiment 1 of the invention.

FIG. 2 is a view showing an example of how a standard sample 6h is divided into regions in embodiment 1 of the invention. Although the size and shape of each region obtained by the division can be specified at will, the data processing time is preferably set to a bare minimum because the time depends on the number of the regions and on their shape.

The example shown in FIG. 2 is an example of a case where the shape of each region obtained by a division is a square.

Figure 3:
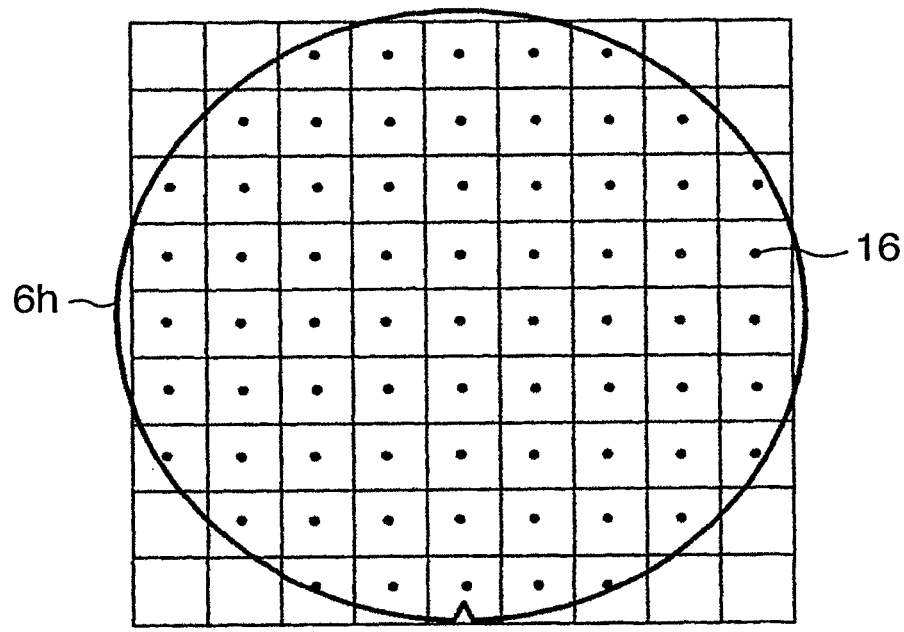
FIG. 3 is an explanatory view of artificial defects on a standard sample in embodiment 1 of the invention.

FIG. 3 is a view showing an example in which defects are formed on the standard sample 6h in embodiment 1 of the present invention. In the example of FIG. 3, artificial defects 16 are disposed at known positions which are spaced at equal intervals like a grid (i.e., defects of previously known coordinates are formed). The shape, size, and positions of the defects are so set that they can be detected using scattering light.

Note that at least one defect is formed in each region of the grid-like area.

Preferably, the size and shape of each artificial defect 16 are set at will according to the purpose of use. The artificial defects 16 are formed by a focused ion beam (FIB) instrument.

Figure 4:
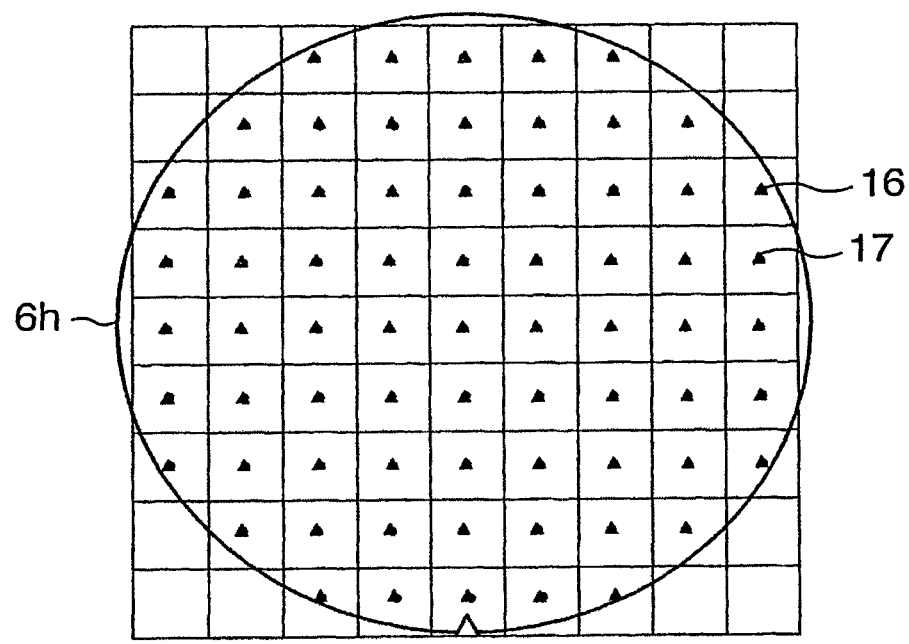
FIG. 4 is an explanatory view of the difference between the artificial defects on the standard sample in embodiment 1 of the invention and an image of detected defects.

FIG. 4 is a view showing the results of an inspection of the artificial defects machined or processed in the standard sample 6h in embodiment 1 of the invention. In FIG. 4, the artificial defects 16 and detected defects 17 are simultaneously shown.

Figure 5:
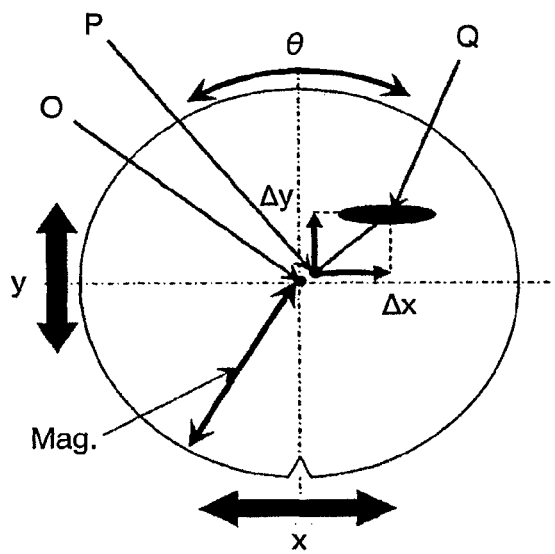
FIG. 5 is an explanatory view of information that is discernible from the image of detected defects in embodiment 1 of the invention.

FIG. 5 is a diagram illustrating positional deviation information that is found from the results of an inspection of the standard sample 6h in embodiment 1 of the present invention. In FIG. 5, the O indicates the center of the object to be inspected. The P indicates the center of the rotary stage. The Q indicates the position of the center of the beam. The Δx and Δy are amounts of deviation of the beam position. The Δx indicates the deviation between the center of the rotary stage and the position of the beam center, taken in the X-direction. The Δy indicates the deviation between the center of the rotary stage and the central position of the beam, taken in the Y-direction. The θ, x, and y are the amounts of deviation of the position into which the wafer is carried. The θ indicates the amount of deviation in the rotational direction. The offset x indicates the amount of deviation of conveyance in the X-direction (wafer shift in the X-direction). The offset y indicates the amount of deviation of conveyance in the Y-direction (wafer shift in the Y-direction). The Mag. is an amount of elongating or shrinking deviation and indicates the magnification error (error in the stage scale) in the R-direction.

In FIG. 5, the amount of deviation in the rotational direction, the amount of elongating or shrinking deviation (magnification), the amounts of offset deviations (conveyance errors), and the amounts of deviation of the optical axis that are parameters are obtained from the results of the inspection. That is, parameter information is obtained. For example, by correcting the parameters, information about the detection position obtained from the inspected object 6 by the review device is used as reference data. The results of an inspection obtained by a defect inspection device are matched with the reference data, and the detection position can be corrected.

Figure 6:
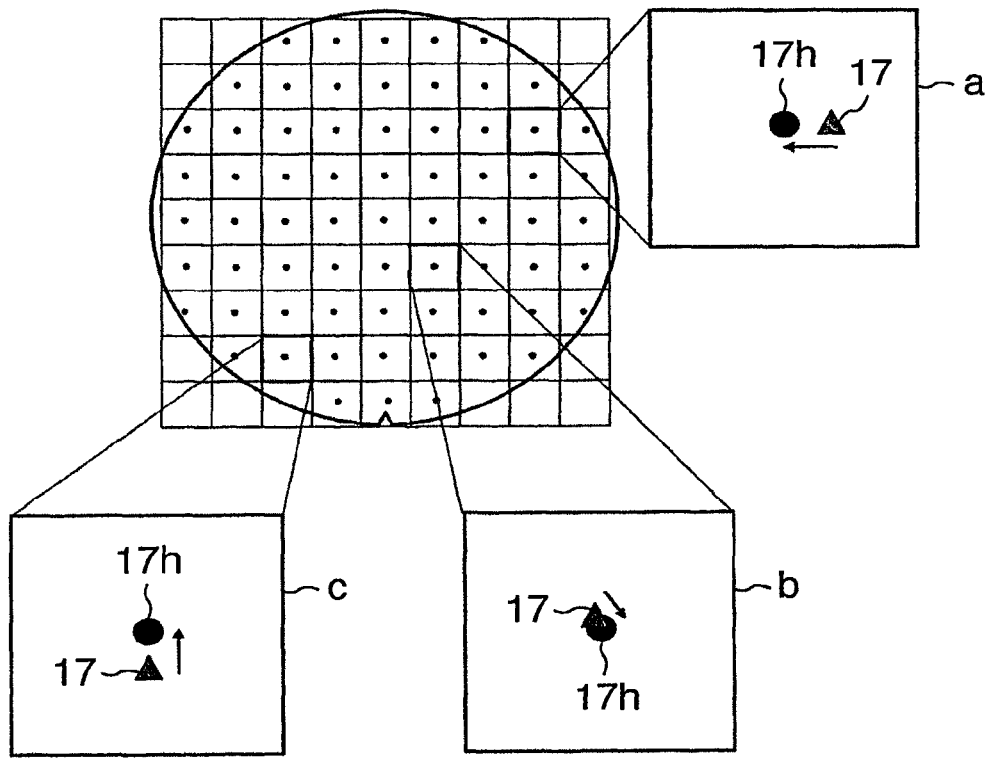
FIG. 6 is an explanatory view of a case in which a fine adjustment is made after a rough adjustment in embodiment 1 of the invention.

FIG. 6 is a view illustrating a method consisting of making rough adjustments using the parameters (all the coordinates are corrected (e.g., all the coordinates are corrected by moving them in the X- (-Y)-axis direction)), then dividing the inspected object 6 like a grid into regions, and making fine adjustments of positional coordinates in each region (a positional adjustment is made independent of other regions). Errors that cannot be fully corrected with rough adjustments (such as waviness of the sample) can be corrected with these fine adjustments. Consequently, errors can be reduced.

For example, where the detection position after a rough correction is as shown in FIG. 6, a defect 17 existing in a region a is finely corrected to a position 17h in the direction of the arrow. Similarly, in regions b and c, fine corrections are made in the directions of the arrows. The positions of defects can be detected more accurately by making a fine correction in each region over the whole surface of the inspected object 6.

Figure 7:
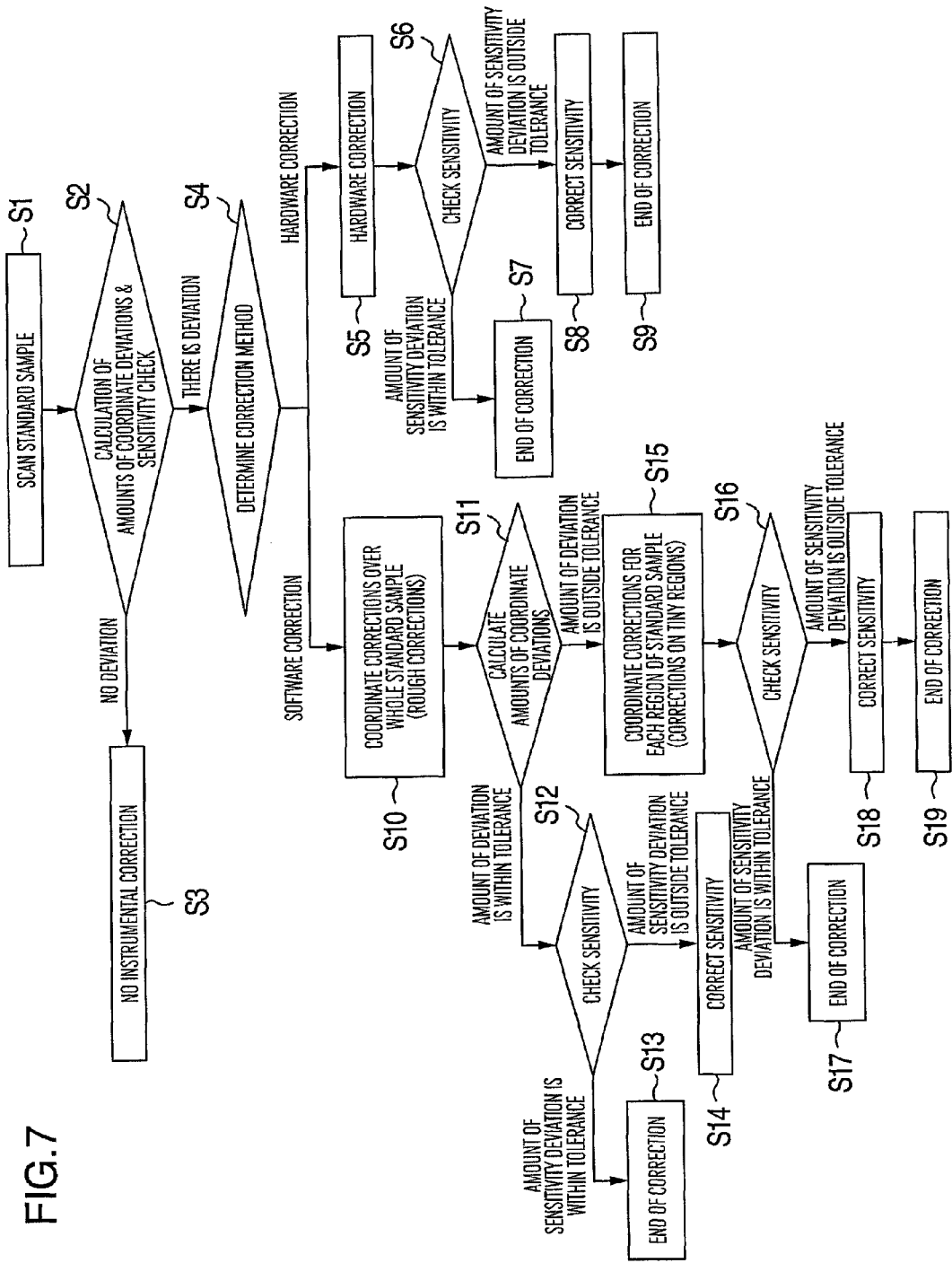
FIG. 7 is a flowchart of operations in embodiment 1 of the invention.
Figure 8:
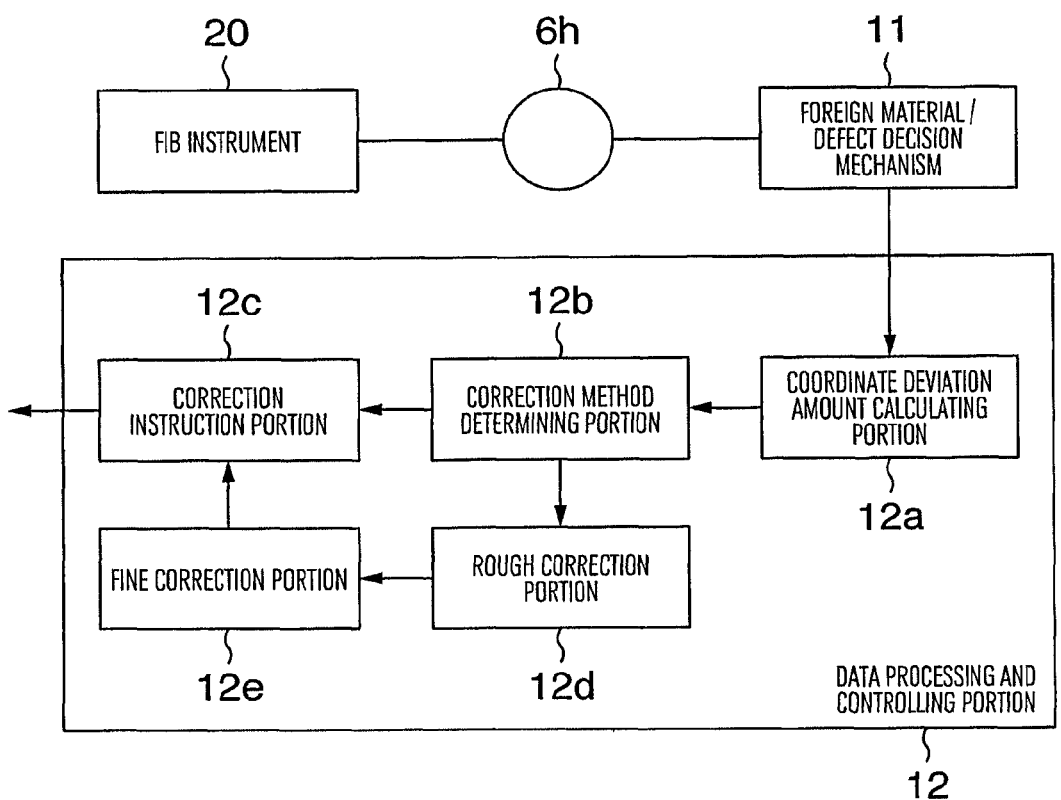
FIG. 8 is a functional block diagram of a data processing and controlling portion in embodiment 1 of the invention.

FIG. 7 is a flowchart of operations for position corrections made by the defect inspection device in embodiment 1 of the present invention. FIG. 8 is a functional block diagram of a data processing and controlling portion that carries out the flow of operations illustrated in FIG. 7.

In step S1 of FIG. 7, artificial defects are formed on the standard sample 6h by FIB 20. A decision is made regarding defects by the foreign material/defect decision mechanism 11. Defect data is supplied to a coordinate deviation amount calculating portion 12a of the data processing and controlling portion 12.

In step S2, the coordinate deviation amount calculating portion 12a calculates the amount of coordinate deviations between each artificial defect 16 on the standard sample 6h and the detected defect 17 and checks the sensitivity (instrumental sensitivity (luminance, brightness, or the like)). If there is no deviation in the coordinate position or if the coordinate position deviation is within a given range, no instrumental correction is made (step S3).

In a case where the deviation of the coordinate position is more than the given value in step S2, a correction method determining portion 12b determines a method of correction (step S4). If the coordinate deviation is in excess of a certain value in step S4, control goes to execution of the hardware correction (mechanical or optical adjustment of a mechanism for detecting scattering light). If the coordinate deviation is less than the certain value, a software correction is carried out.

If the decision at step S4 is that a hardware correction is needed, control goes to step S5, where a correction instruction portion 12c supplies correction instruction signals to the brightness correcting mechanism 2, the optical axis correcting mechanism 3, and so on. Control then goes to step S6, where the correction instruction portion 12c checks the aforementioned sensitivity. If it is within an allowable value, the correction is ended (step S7).

If the amount of sensitivity deviation is in excess of the allowable value in step S6, control proceeds to step S8, where the correction instruction portion 12c supplies a correction instruction signal to the brightness correcting mechanism 2 or the like to correct the sensitivity, and then the correction is ended (step S9).

If the decision at step S4 is that the correction can be made by a software correction, control goes to step S10, where a rough correction portion 12d corrects the coordinates over the whole standard sample (rough corrections).

Then, control goes to step S11, where the rough correction portion 12d calculates the amount of the coordinate deviation and makes a decision as to whether or not the calculated amount of deviation is within a tolerable value. If the calculated amount of deviation is within the tolerable value, the rough correction portion 12d checks the sensitivity in step S12. If the amount is within the tolerable value, control passes to step S13, where the correction is ended.

If the checked sensitivity is outside the tolerance in step S12, the rough correction portion 12d corrects the sensitivity in step S14.

If the calculated amount of coordinate deviation is outside the tolerance in step S11, control goes to step S15, where a fine correction portion 12e corrects the coordinates in each region obtained by dividing the standard sample 6h.

In step S16, the sensitivity is checked. If the amount of coordinate deviation is within the tolerable value, the correction is ended in step S17.

If the amount of sensitivity deviation is outside the tolerable value in step S16, the sensitivity is corrected in step S18, and the correction is terminated (step S19).

As described previously, in embodiment 1 of the present invention, the coordinates of the detected defect can be detected by inspecting the standard sample 6h on which the artificial defects 16 are disposed.

Since the artificial defects 16 on the standard sample 6h have a known size (brightness) and are located in known positions, it follows that stage position information, conveyance error, beam position on the sample, and detected brightness information can be obtained by detecting the standard sample 6h.

A correction either of an in-plane distribution across the inspected object or of brightnesses (sizes) can be made, as well as a correction of the detection position, by providing feedback control of the correction mechanism portions including the sample transport portion 13 and the stage portion 7 based on these types of information so as to correct the coordinate positions.

Figure 9:
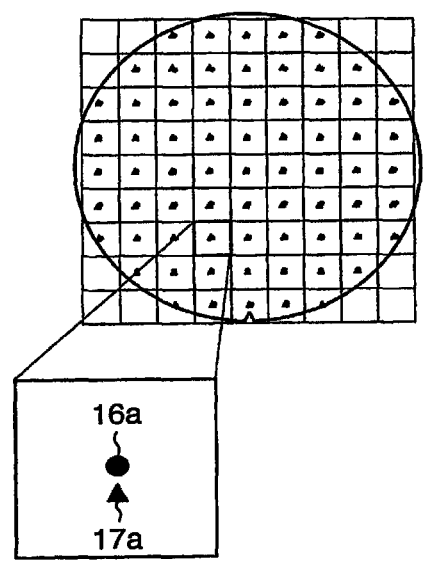
FIG. 9 is an explanatory view illustrating the manner in which the magnitude of an inspection result can be corrected by making a brightness correction in embodiment 1 of the invention.

For example, as shown in FIG. 9, in a case where the size of each artificial defect 16a is 50 nm and the size of a detected defect 17a, i.e., inspection result, is 46 nm, the detected defect 17a, i.e., the detection result, can be corrected to 50 nm by making a correction to the detection result or enhancing the brightness by the brightness correction mechanism. The sensitivity decrease due to an aging variation of the instrument can be corrected for each inspection of the standard sample. Stable state of operation of the instrument can be maintained at all times.

Figure 10:
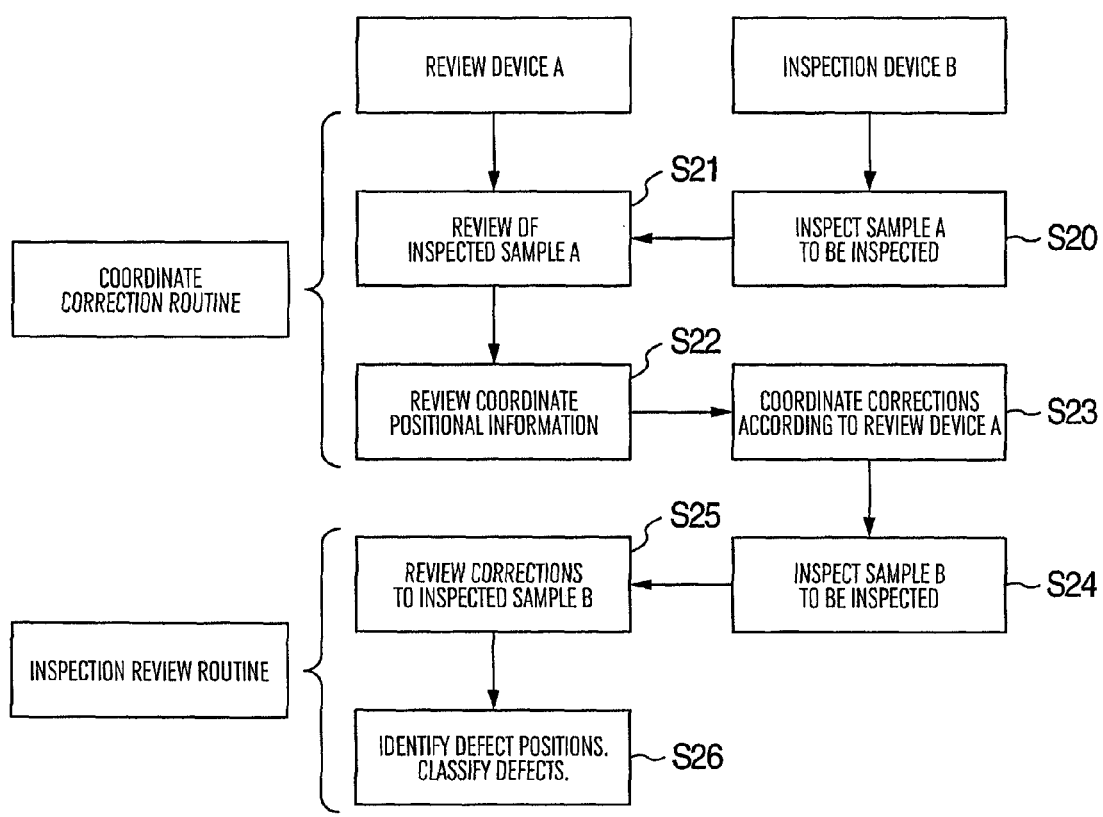
FIG. 10 is a flowchart schematically illustrating the whole operation of a comparative example that is an example different from the invention.

FIG. 10 is a flowchart of the whole operation of an example of a case in which corrections are made and defects are confirmed without using any standard sample, unlike the present invention, and is a chart showing one example for comparison with the present invention.

Figure 11:
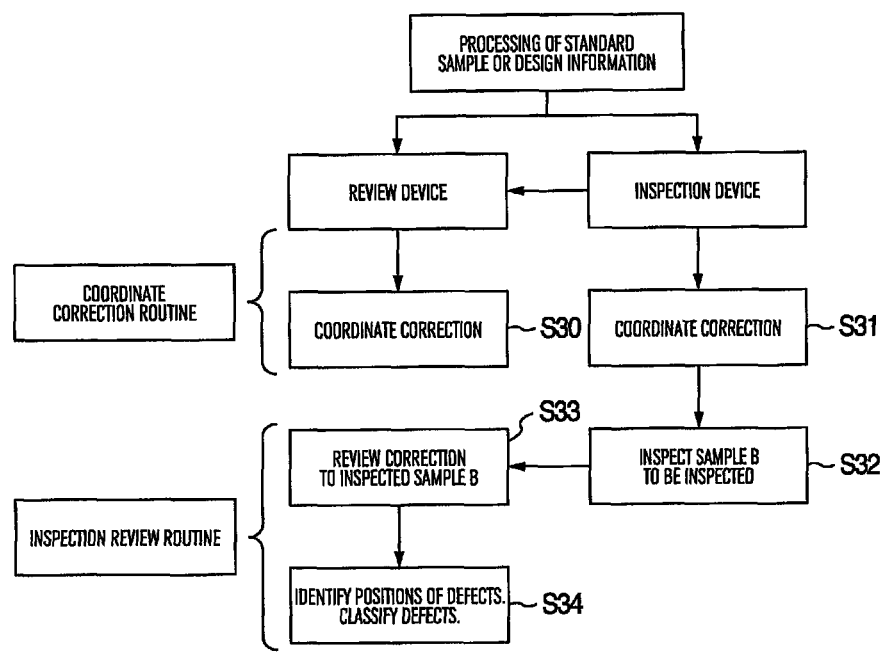
FIG. 11 is a flowchart schematically illustrating the whole operation in the present invention.

FIG. 11 is a flowchart of the whole operation in a case where corrections are made and defects are confirmed using a standard sample in accordance with an embodiment of the present invention.

In FIG. 10, a sample A to be inspected is inspected by an inspection device B (step S20). The inspected sample A is reviewed with a review device A (step S21).

And, coordinate position information about the inspected sample A is obtained by the review device A (step S22).

Subsequently, coordinate corrections are made by the inspection device B according to the coordinate position information derived by the review device A (step S23).

Then, the inspection device B inspects the inspected sample B using the corrected coordinates (step S24). The review device A makes a review correction of the inspected sample B (step S25). The positions of defects are identified and the defects are classified (step S26).

In the example shown in FIG. 10, coordinate position information about the inspected sample A is obtained by the review device A, and the coordinates of the inspection device B are corrected according to the information. Accordingly, the sample inspected by the inspection device B must be reviewed by the review device A. Where other review device is used, it is necessary that a sample inspected by the inspection device B be newly reviewed and that coordinate position information be obtained.

In contrast, in the case of the present invention shown in FIG. 11, coordinate corrections are made while both inspection device and review device use a standard sample. Therefore, defects can be inspected with no restrictions on the inspection device or on the review device.

That is, in FIG. 11, coordinate corrections are made to the standard sample on which a defect is formed, by the use of a review device and an inspection device (steps S30 and S31). Consequently, the review device and the inspection device share common coordinates.

The inspection device inspects the inspected sample B (step S32). The review device makes a review correction to the inspected sample B (step S33), identifies the positions of defects, and classifies the defects (step S34).

FIB processing or stepper photolithography is used for the standard sample used in the present invention, and defects are formed. With these methods of processing, it is easy to obtain information about the positions at which artificial defects are processed, as well as design information.

In the example shown in FIG. 10, it is necessary to make coordinate corrections while moving the inspected sample A to and fro between the inspection device and the review device. Hence, a long time is also required to make coordinate corrections.

In the present invention, if each of the inspection device and the review device makes coordinate corrections based on processing information or design information through the use of processing information and design information about the standard sample, a line can be built in which any review device can observe defects with equal performance without identifying the review device relative to the inspection device.

Because the coordinate accuracy is improved, defects closely spaced from each other can be separated. It is easy to grasp the shapes of defects. When defect kinds are classified, the classification accuracy is improved.

Defects can be separated from each other. Variations in the number of detected defects are suppressed. Variations among individual machines can be reduced.

Because conveyance errors and optical axis deviation in a defect detection device can be corrected, the stability of the instrument can be improved. Management of the state of the instrument can be facilitated. Stable state of the inspection device can be accomplished.

Since the coordinate accuracy in the defect detection device is improved, the observation time of the defect review device is reduced. Also, the observation accuracy is improved. Therefore, an improvement in the yield in semiconductor manufacturing steps can be accomplished.

Processing position information about a standard sample and design values are previously available by using an inspected object having artificial defects disposed at known positions over the whole surface of the object as a wafer for calibration of standard coordinates. Therefore, no corrections are necessary after the inspection device and the review device perform an inspection and a review, respectively. This leads to a great decrease in time.

Furthermore, coordinate errors in plural instruments can be eliminated. A line can be built in which observations can be made with no restrictions on the review device.

Figure 12:
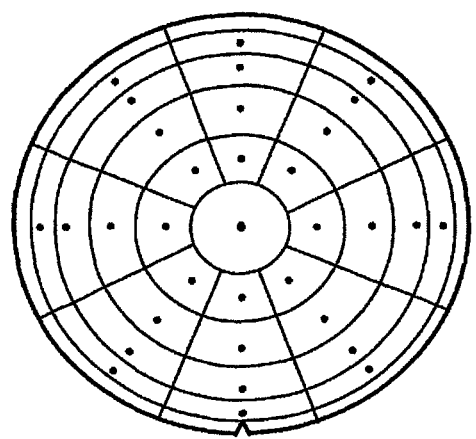
FIG. 12 is a view showing another method of dividing a standard sample.

Additionally, the example shown in FIG. 2 shows an example in which the standard sample 6h is divided into plural squares of the same area. As shown in FIG. 12, the sample may be divided into plural concentric circles which in turn are divided by plural lines extending radially. Further, the sample may be divided into plural squares, and the square corresponding to the central portion of the standard sample 6h may have a larger area, while surrounding squares may have a smaller area.

Although the foregoing description has been provided regarding the embodiment, the present invention is not restricted thereto. It is obvious to those skilled in the art that various changes and modifications are made within the spirit of the present invention and the scope of the accompanying drawings.

REFERENCE SIGNS LIST

1: light source
2: brightness correcting mechanism
3: optical axis correcting mechanism
4a-4c: mirrors
5a, 5b, 8: condenser lenses
6: sample
6h: standard sample
7: XZ seater stage
9: detector
10: amplifier
11: foreign material/defect decision mechanism
12: data processing and controlling portion
12a: coordinate deviation amount calculating portion
12b: correction method determining portion
12c: correction instruction portion
12d: rough correction portion
12e: fine correction portion
13: sample transport portion
16: artificial defects
17: detected defect
20: FIB instrument

What we claim is:

1. An inspection apparatus comprising:
an optical system configured to illuminate light to a standard sample having plural artificial defects disposed at known positions;
a detector configured to detect scattered light from the standard sample;
a determination unit configured to detect the artificial defects based on a signal from the detector; and
a data processing unit configured to compare a coordinate position of the artificial defects outputted from the determination unit and the known positions, and to correct a coordinate deviation based on a result of the comparison;
wherein the data processing unit is configured to divide the whole standard sample into plural regions, and
wherein the data processing unit is configured to perform fine adjustments to correct the coordinate deviation for each of the regions, obtained by the division of the whole standard sample based on the result of the comparison for each of the plural artificial defects.

2. The inspection apparatus according to claim 1, wherein a correction amount for each of the regions obtained by the division is determined independent of a correction amount for other regions obtained by the division.

3. The inspection apparatus according to claim 1, wherein rough adjustments to correct a coordinate deviation in a same direction over the whole standard sample are performed before the fine adjustments.

4. The inspection apparatus according to claim 3, wherein at least one of an amount of deviation in a rotational direction, an amount of elongating or shrinking deviation, an amount of conveyance errors deviations, and an amount of deviation of an optical axis is corrected by the rough adjustments.

5. The inspection apparatus according to claim 1, wherein the standard sample is divided into grid-like areas.

6. The inspection apparatus according to claim 1, wherein the standard sample is divided into concentric areas and divided by plural lines extending radially.

7. The inspection apparatus according to claim 1, wherein one defect is included in each of the region obtained by the division.

8. The inspection apparatus according to claim 1, wherein a first region of the regions obtained by the division includes a first artificial defect;

wherein a second region of the regions obtained by the division includes a second artificial defect;

wherein a third region of the regions obtained by the division includes a third artificial defect; and wherein an interval between the first artificial defect and the second artificial defect is equal to an interval between the second artificial defect and the third artificial defect.

9. The inspection apparatus according to claim 1, wherein the determination unit comprises a foreign material/defect decision unit configured to record coordinates of positions at which the scattered light is detected, and wherein the data processing unit comprises a data processing and controlling portion configured to analyze positions, sizes and shapes of the detected artificial defects and to provide feedback control to a stage on which the standard sample is mounted based on the corrected coordinate deviation determined by the determination unit.

10. A coordinate adjustment method comprising:
illuminating light to a standard sample having plural artificial detects disposed at known positions;
detecting scattered light from the standard sample;
detecting the artificial defects based on a signal from the detector;
dividing the whole standard sample into plural regions;
comparing a coordinate position of the detected artificial defects and the known positions; and
performing fine adjustments to correct the coordinate deviation for each of the regions, obtained by the division of the whole standard sample based on the result of the comparison for each of the plural artificial defects.

11. The coordinate adjustment method according to claim 10,
wherein a correction amount for each of the regions, obtained by the division is determined independent of a correction amount for other regions obtained by the division.

12. The coordinate adjustment method according to claim 10,
wherein rough adjustments to correct a coordinate deviation in a same direction over the whole standard sample are performed before the fine adjustments.

13. The coordinate adjustment method according to claim 12,
wherein at least one of an amount of deviation in a rotational direction, an amount of elongating or shrinking deviation, an amount of conveyance errors deviations, and an amount of deviation of an optical axis is corrected by the rough adjustments.

14. The coordinate adjustment method according to claim 10,
wherein the standard sample is divided into grid-like areas.

15. The coordinate adjustment method according to claim 10,
wherein the standard sample is divided into concentric areas and divided by plural lines extending radially.

16. The coordinate adjustment method according to claim 10,
wherein one defect is included in each of the region obtained by the division.

17. The coordinate adjustment method according to claim 10,
wherein a first region of the regions obtained by the division includes a first artificial defect;
wherein a second region of the regions obtained by the division includes a second artificial defect;
wherein a third region of the regions obtained by the division includes a third artificial defect; and
wherein an interval between the first artificial defect and the second artificial defect is equal to an interval between the second artificial defect and the third artificial defect.

* * * * *